United States Patent [19]

Tanouchi et al.

[11] 4,346,099
[45] Aug. 24, 1982

[54] CARBOXY-IMIDAZOLE DERIVATIVES, COMPOSITIONS AND USE

[75] Inventors: Tadao Tanouchi, Takatsuki; Masanori Kawamura; Takanori Okada, both of Ibaraki; Masaki Hayashi, Takatsuki, all of Japan

[73] Assignees: Ono Pharmaceutical Co., Ltd., Osaka; Kissei Pharmaceutical Co., Ltd., Nagano, both of Japan

[21] Appl. No.: 304,531

[22] Filed: Sep. 22, 1981

[51] Int. Cl.³ ............................................. A61K 31/415
[52] U.S. Cl. .................................. 424/273 R; 548/341
[58] Field of Search ............................... 548/341, 335; 424/273 R

[56] References Cited

U.S. PATENT DOCUMENTS 4,073,923  2/1978  Balasubramenyan et al. ...... 548/341

FOREIGN PATENT DOCUMENTS 1925994  11/1970  Fed. Rep. of Germany .

Primary Examiner—Robert W. Ramsuer

Attorney, Agent, or Firm—Sughrue, Mion, Zinn, Macpeak & Seas

[57] ABSTRACT

The imidazole derivatives of the general formula:

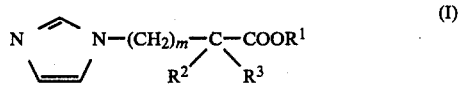

(I)

[wherein m represents an integer of 4 to 9, $R^1$ represents a hydrogen atom or a straight- or branched-chain alkyl group containing from 1 to 12 carbon atoms, and one of $R^2$ and $R^3$ represents a hydrogen atom, and the other represents a halogen atom or a phenyl group, or $R^2$ and $R^3$ together represent $-(CH_2)_n-$ (in which n represents an integer of 4 to 6) or represent $=CH_2$] and non-toxic salts thereof, which have a specifically inhibitory effect on the biosynthesis of thromboxane $A_2$ (abbreviated as $TXA_2$ hereafter) and are, therefore, useful as treating agents for diseases caused by $TXA_2$ such as inflammation, cerebral apoplexy, myocardial infarction, acute cardiac death, cardiostenosis and thrombus etc.

12 Claims, No Drawings

CARBOXY-IMIDAZOLE DERIVATIVES, COMPOSITIONS AND USE

The present invention is concerned with new imidazole derivatives and pharmaceutical compositions containing them.

Up to now, as compounds having an inhibitory active on the biosynthesis of $TXA_2$, (i) sodium p-benzyl-4-[1-oxo-2-(4-chlorobenzyl)-3-phenylpropyl]phenylphosphonate (N-0164), (ii) 2-isopropyl-3-nicotinylindole (L-8027), (iii) 9,11-epoxymethanoprostanoic acid and (iv) imidazole etc. [cf. Annual Review of Biochemistry 47, 1002–1004 (1978)] have been known.

Furthermore, it has recently found that imidazole derivatives having various substituents at the 1-position thereof, possess a strong inhibitory effect on the biosynthesis of $TXA_2$. (cf. our British Pat. Nos. 2016452A, 2024807A, 2025946A and 2031408A).

The present inventors have conducted extensive investigations in order to discover a new imidazole derivative which strongly inhibits the biosynthesis of $TXA_2$, and have found that the imidazole derivatives of the present invention achieve the objects and thus completed the present invention.

Accordingly, the present invention provides new imidazole derivatives of the general formula:

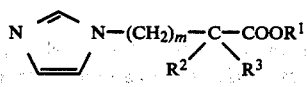
(I)

[wherein m represents an integer of 4 to 9, $R^1$ represents a hydrogen atom or a straight- or branched-chain alkyl group containing from 1 to 12 carbon atoms, and one of $R^2$ and $R^3$ represents a hydrogen atom, and the other represents a halogen atom or a phenyl group, or $R^2$ and $R^3$ together represent $-(CH_2)_n-$ (in which n represents an integer of 4 to 6) or represent $=CH_2$] and non-toxic salts thereof, which have a specifically inhibitory effect on the biosynthesis of thromboxane $A_2$ (abbreviated as $TXA_2$ hereafter) and are, therefore, useful as treating agents for diseases caused by $TXA_2$ such as inflammation, cerebral apoplexy, myocardial infarction, acute cardiac death, cardiostenosis and thrombus etc.

Examples of the straight- or branched-chain alkyl group containing from 1 to 12 carbon atoms represented by $R^1$, are methyl, ehtyl, propyl, butyl, pentyl, hexyl, heptyl, octyl, nonyl, decyl, undecyl, dodecyl and their isomers. Preferably $R^1$ is a hydrogen atom or a straight- or branched-chain alkyl group containing from 1 to 4 carbon atoms, most preferably a hydrogen atom or a methyl or ethyl group.

Example of the alkylene group represented by $-(CH_2)_m-$ is tetramethylene, pentamethylene, hexamethylene, heptamethylene, octamethylene and nonamethylene. Preferably $-(CH_2)_m-$ is pentamethylene, hexamethylene or heptamethylene, most preferably hexamethylene.

According to a feature of the present invention, compounds of general formula (I) wherein one of $R^2$ and $R^3$ represents a hydrogen atom, and the other represents a phenyl group, or $R^2$ and $R^3$ together represent $-(CH_2)_n-$, and the other symbols are as hereinbefore defined, i.e. compounds of the general formula:

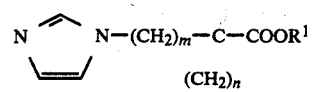
(IA)

or

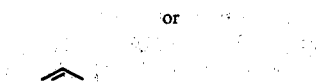
(IB)

[wherein all of the symbols are as hereinbefore defined] may be prepared by reacting an imidazole metal salt e.g. a silver salt, or an alkali metal salt with a halogen compound represented of the general formula:

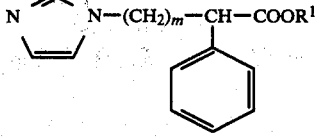
(IIA)

or

(IIB)

[wherein X represents a halogen atom and the other symbols are as hereinbefore defined].

As reaction solvents used in the above reaction, there may be used any one that does not influence the reaction, being usually benzene, toluene, xylene, N,N-dimethylformamide, acetonitrile or a lower alcohol etc. The reaction may be carried out at a temperature from 0° C. to 150° C., usually from room temperature to a reflux temperature of reaction solvent.

Compounds of general formula (I) wherein one of $R^2$ and $R^3$ represents a hydrogen atom, and the other represents halogen atom, and the other symbols are as hereinbefore defined, i.e. compounds of the general formula:

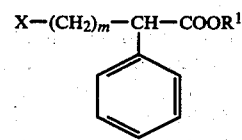
(IC)

[wherein all of the symbols are as hereinbefore defined] may be prepared by halogenating an alcohol compound of the general formula:

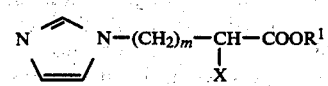
(III)

[wherein all of the symbols are hereinbefore defined].

The reaction is carried out by conventional methods for converting an alcohol compound into a halogen compound, e.g. with a halogen acid such as hydrobromic acid or thionyl chloride.

Compounds of general formula (III) may be prepared from compounds of the general formula:

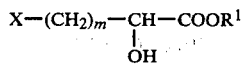 (IIC)

[wherein all of the symbols are as hereinbefore defined] by means hereinbefore mentioned for obtaining compounds of the general formula (IA) or (IB).

Compounds of general formula (I) wherein $R^2$ and $R^3$ together represent $=CH_2$ and the other symbols are as hereinbefore defined, i.e. compounds of general formula:

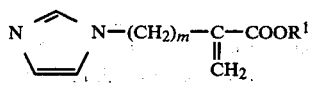 (ID)

[wherein all of the symbols are as hereinbefore defined] may be prepared by dehydrating an alcohol of general formula:

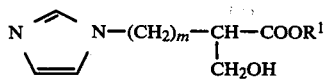 (IV)

[wherein all of the symbols are as hereinbefore defined].

The reaction is carried out by conventional dehydration using an acid catalyst for obtaining an olefin compound, preferably using phosphoric acid under reduced pressure at a temperature from 150° C. to 180° C.

Compounds of general formula (IV) may be prepared from compounds of the general formula:

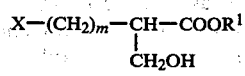 (IID)

[wherein all of the symbols are as hereinbefore defined] by the method described above for the preparation of the compounds of general formula (IA) or (IB).

Compounds of general formula (IA), (IB), (IC), (ID), (III) or (IV) wherein $R^1$ is a hydrogen atom and the other symbols are as hereinbefore defined, may also be prepared by hydrolysing compounds of general formula (IA), (IB), (IC), (ID), (III) or (IV) wherein $R^1$ is a straight- or branched-chain alkyl group containing from 1 to 12 carbon atoms and the other symbols are as hereinbefore defined under alkaline conditions.

The hydrolysis is carried out in an aqueous solution of hydroxide or carbonate of an alkaline metal such as sodium or potassium, in the presence or absence of a water-miscible solvent, e.g. an ether such as tetrahydrofuran or a lower alcohol such as methanol or ethanol.

Compounds of general formula (I) wherein $R^1$ represents a straight- or branched-chain alkyl group containing from 1 to 12 carbon atoms and the other symbols are as hereinbefore defined, may also be prepared esterifying compounds of general formula (I) wherein $R^1$ represents a hydrogen atom and the other symbols are as hereinbefore defined, by known method of esterification of a carboxylic acid to a ester, for example, the method using a diazoalkane.

The compounds of general formula (I) are purified by conventional methods, for example, distillation under normal pressure or reduced pressure, or high speed liquid chromatography, thin layer chromatography or column chromatography on silica gel or recrystallization.

Imidazole metal salts may be prepared by reacting an imidazole with an alkali metal hydride such as sodium hydride, an alkali metal alcoholate such as sodium methoxide, an alkali metal carbonate such as sodium or potassium carbonate, an alkali metal hydroxide such as sodium or potassium hydroxide, or a silver oxide in an inert solvent. These metal salts may be used as isolated compounds or as a solution of the salts.

The halogen compounds of general formula (II) are known per se or prepared by known methods. For example, compounds of general formula (IIA), (IIB) or (IID) may be prepared by reacting compounds of the general formula:

 (V)

[wherein one of $R^4$ and $R^5$ represents a hydrogen atom, the other represents a phenyl group or a hydroxymethyl group, or $R^4$ and $R^5$ together represent $-(CH_2)_n-$; $R^1$ and n are as hereinbefore defined] using a lithioating agent such as butyl lithium or lithium diisopropylamide, to obtain a lithium compound, and reacting the resulting compound with halogen compounds of the general formula:

$$X-(CH_2)_m-X \quad (VI)$$

[wherein X and m are as hereinbefore defined].

The reaction is carried out in an inert organic solvent for example, tetrahydrofuran, diethyl ether, hexane or hexamethylphosphamide, or the mixture of two or more of them at a low temperature from $-78°$ C. to room temperature.

The compounds of general formula (IIC) may be prepared by the series of reactions depicted schematically below.

SCHEME

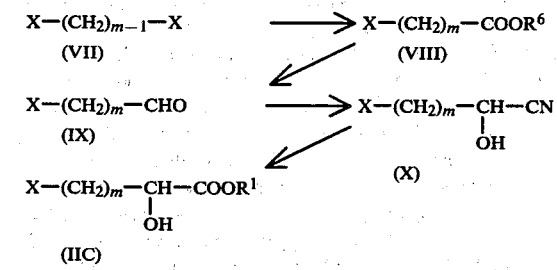

wherein, $R^6$ represents a straight- or branched-chain alkyl group containing from 1 to 4 carbon atoms, the other symbols are as hereinbefore defined.

Referring to the scheme, compounds of general formula (VIII) may be prepared from compounds of general formula (VII) and compounds of general formula: $CH_3COOR^6$ (wherein $R^6$ are as hereinbefore defined), by the method described above for the preparation of compounds of general formula (IIA), (IIB) or (IID). Compounds of general formula (IX) are prepared from the compounds of general formula (VIII) by methods known per se for converting a ester of carboxylic acid into a formyl group, for example, using diisobutyl aluminium hydride. Aldehyde compounds of general formula (IX) thus obtained, may be converted into compounds of general formula (X) by methods known per se, and compounds of general formula (X) may hydrolyzed and, if desired, esterified to obtain compounds of general formula (IIC).

Acid addition salts of imidazole derivatives of general formula (I) may be prepared from the compounds of general formula (I) by methods known per se, for example, by reaction of stoichiometric quantities of a compound of general formula (I) and an appropriate acid, e.g. an inorganic acid such as hydrochloric acid, hydrobromic acid, hydroiodic acid, sulphuric acid, phosphoric acid or nitric acid, or an organic acid such as acetic acid, lactic acid, tartaric acid, benzoic acid, citric acid, methanesulphonic acid, ethanesulphonic acid, benzenesulphonic acid, toluenesulphonic acid or isethionic acid, in a suitable solvent.

Neutral salts may be prepared from the acids of general formula (I) wherein $R^1$ represents a hydrogen atom, by methods known per se, for example, by reaction of stoichiometric quantities of an acid of general formula (I) and an appropriate base, e.g. an alkali metal or alkaline earth metal hydroxide or carbonate, or an organic amine, in a suitable solvent. Preferably acid addition salts and neutral salts are non-toxic salts.

By the term 'non-toxic salts' as used in this specification, is meant salts the anions or cations of which are relatively innocuous to the animal organism when used in therapeutic doses so that the benefitical pharmacological properties of the compounds of general formula (I) are not vitiated by side effects ascriable to those anions or cations. Preferably the salts are water-soluble.

Suitable acid addition salts of imidazole derivatives are, for example, inorganic acid salts such as hydrochloride, hydrobromide, hydroiodide, sulfate, phosphate, nitrate, or organic acid salts such as acetate, lactate, tartarate, benzoate, citrate, methanesulphonate, ethanesulphonate, benzenesulphonate, toluenesulphonate or isethionate.

Suitable neutral salts include the alkali metal, e.g. sodium or potassium salts, the alkaline earth metal, e.g. calcium or magnesium salts and ammonium salts, and pharmaceutically acceptable (i.e. non-toxic) amine salts. Amines suitable for forming such salts with calboxylic acids are well known and include, for example, amines derived in theory by the replacement of one or more of the hydrogen atoms of ammonia by groups, which may be the same or different when more than one hydrogen atom is replaced, selected from, for example, alkyl groups containing from 1 to 6 carbon atoms and hydroxyalkyl groups containing from 2 or 3 carbon atoms.

Suitable non-toxic amine salts are, e.g. tetraalkylammonium salts such as tetramethylammonium salts, and the other organic amine salts such as methylamine salts, dimethylamine salts, cyclopentyl amine salts, benzylamine salts, phenetylamine salts, piperidine salts, monoethanolamine salts, diethanolamine salts, lysine salts and arginine salts.

The imidazole derivatives of general formula (I) and non-toxic salts thereof possess an inhibitory effect on the biosynthesis of $TXA_2$, and are, therefore, useful for controlling the biosynthesis of $TXA_2$ in mammals including humans when it is desired.

For example, in standard laboratory tests, 1-(7-carboxy-7-chloroheptyl)imidazole hydrochloride, 1-(7-carboxy-7-phenylheptyl)imidazole hydrochloride, 1-(7-carboxy-7,7-pentanoheptyl)imidazole hydrochloride, 1-(7-carboxy-7-octenyl)imidazole hydrochloride produce a 50% inhibition of thromboxane synthetase from rabbit platelet microsomes at the molar concentrations of $2.5 \times 10^{-8}$, $3.8 \times 10^{-8}$, $4.6 \times 10^{-8}$ and $1.6 \times 10^{-8}$, respectively.

To control the biosynthesis of $TXA_2$ is useful for the prevention and treatment of inflammation, cerebral apoplexy, myocardial infarction, acute cardiac death, cartiostenosis and thrombus in mammals including humans, especially in humans. For such purpose, the compounds of the present invention are usually administered systemically, for example, orally, rectally or parenterally.

Doses are determined depending upon age, symptoms, the desired therapeutic effect, the route of administration, the duration of the treatment and the like, and are generally and preferably about 10 mg to 1 g for oral administration, and 0.01 mg to 10 mg for intravenous injection or 1 μg to 100 μg/hour for continuous intravenous infusion, specially when required emargency treatment.

It was confirmed that the value of $LD_{50}$ is more than 5,000 mg/kg by oral administration to rats concerning to the toxicity of compounds of the present invention and therefore, these compounds are considered to be usable enough as pharmaceuticals.

Solid compositions for oral administration include compressed tablets, pills, dispersible powders and granules. In such solid compositions, one or more of the active compounds is or are, admixed with at least one inert diluent such as calsium carbonate, potato starch, alginic acid or lactose. The compositions may also comprise, as is normal practice, additional substances other than inert diluents, e.g. lubricating agents such as magnesium stearate. Liquid compositions for oral administration include pharmaceutically acceptable emulsions, solutions, suspentions, syrups and elixirs containing inert diluents commonly used in the art, such as water or liquid paraffin.

Besides inert diluents such compositions may also comprise adjuvants such as wetting and suspending agents, and sweetening, flavouring, perfuming and preservating agents.

The compositions according to the invention for oral administration, also include capsules of absorbable materials such as gelatin containing one or more of the active substances with or without the addition of diluents or excipients.

Solid compositions for intrarectal administration include suppositories formulated in manner known per se and containing one or more of the active compounds.

Preparation according to invention for parenteral administration include sterile aqueous or non-aqueous solutions, suspensions or emulsions. Example of non-aqueous solvents or suspending media are propylene glycol, polyethylene glycol, vegetable oils such as olive oil, and injectable organic esters such as ethyl oleate. These compositions may also include adjuvants such as preserving, wetting, emulsifying and dispersing agents. They may also be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

The following Reference Examples and Examples illustrate, but not limit, the preparation of compounds of the present invention. In the Reference Examples and Examples, 'TLC', 'IR', 'NMR', 'MS' represent respectively, 'Thin layer chromatography', 'Infrared absorption spectrum', 'Nuclear magnetic resonance spectrum' and 'Mass spectrum'. Where solvent ratios are specified in chromatographic separations, the ratios are by volume: the solvents in parentheses in thin layer chromagraphy show the developing solvent used. Except when specified otherwise, infrared spectra are recorded by the liquid film method, and nuclear magnetic resonance spectra are recorded in deuterochloroform ($CDCl_3$) solution.

REFERENCE EXAMPLE 1

7-bromoheptanoic acid t-butyl ester

To 6.94 ml of diisopropylamine in 100 ml of anhydrous tetrahydrofuran was added dropwise 34 ml of a 1.45 M solution of n-butyl lithium in hexane at −70° C. and the mixture was stirred for 15 minutes. To the solution was added dropwise a solution of 6.63 ml of t-butyl acetate in 30 ml of anhydrous tetrahydrofuran and the mixture was stirred for 30 minutes, and then 8 ml of 1,5-dibromopentane in 10 ml of anhydrous tetrahydrofuran were added thereto and the mixture was stirred for 5 minutes. To it was added 17 ml of hexamethylphosphamide, the mixture was stirred at −78° C. for 1 hour and at from −40° C. to −30° C. for 30 minutes. To the reaction mixture was added an aqueous solution of ammonium chloride, and was separated aqueous layer from organic layer. The aqueous layer was extracted with diethyl ether, and the extract was added that organic layer and washed with water, a saturated aqueous solution of ammonium chloride, dried over magnesium sulfate and concentrated under reduced pressure. The residue was purified by column chromatography on silica gel using a mixture of methylene chloride and cyclohexane (1:1) as an eluent to give 8.5 g of the title compound having the following physical characteristic:

TLC (benzene): Rf=0.64.

REFERENCE EXAMPLE 2

7-bromoheptanaldehyde

To 8.5 g of 7-bromoheptanoic acid t-butyl ester (prepared as described in Reference Example 1) in 80 ml of methylene chloride was added dropwise 18.2 ml of a 25% solution of diisobutyl alminium hydride in toluene at −78° C. over a period of 1 hours. The solution was stirred at the same temperature, to which was added 5 ml of methanol at from 0° C. to 10° C. and then added 10 ml of water, and the mixture was stirred at 30° C. to 40° C. for 1 hour. The deposited crystals were filtered out, and the filtrate was concentrated under reduced pressure. The residue was purified by column chromatography on silica gel using a mixture of methylene and chloride and cyclohexane (1:1) as an eluent to give 5.28 g of the title compound having the following physical characteristic:

TLC (benzene): Rf=0.44.

REFERENCE EXAMPLE 3

1-bromo-7-hydroxyoctanenitrile

To 253 mg of sodium cyanide in 8.6 ml of water was added 983 mg of the aldehyde (prepared as described in Reference Example 2) and 10 g of ice, and 1.47 ml of a saturated aqueous solution of sodium bisulfate was added dropwise slowly thereto with severe stirring. After stirring vigorously for 1.5 hours, the mixture was extracted with diethyl ether, the organic layer was washed with a saturated aqueous solution of sodium chloride, dried over magnesium sulfate and concentrated under reduced pressure to give 560 mg of the title compound having the following physical characteristic:

TLC (benzene:ethyl acetate=2:1): Rf=0.56.

REFERENCE EXAMPLE 4

8-bromo-2-hydroxyoctanoic acid methyl ester

To 560 mg of the nitrile (prepared as described in Reference Example 3) was added one ml of a 47% aqueous solution of hydrobromic acid, the mixture was stirred at 70° C. to 80° C. for 1 hour, and extracted with ethyl acetate. The extract was dried over magnesium sulfate and concentrated under reduced pressure. To the obtained residue was added 2 ml of diethyl ether, and a solution of diazomethane in diethyl ether was added thereto till insoluble materials were not found. The reaction mixture was concentrated and the residue was purified by column chromatography on silica gel using a mixture of ethyl acetate and benzene (1:10) as an eluent to give 188 mg of the title compound having the following physical characteristics:

TLC (benzene:ethyl acetate=4:1): Rf=0.44;
IR: $\nu$=3500, 2950, 2870, 1740 $cm^{-1}$;
NMR: $\delta$=4.4-4.0 (1H,m), 3.7 (3H,s), 3.3 (2H,t), 3.0 (1H,d), 2.3-1.0 (10H,m);
MS (%): m/e=254 (M+), 252 (M+), 195 (86), 193 (86), 95 (100), 90 (20), 69 (28), 56 (21), 54 (47).

REFERENCE EXAMPLE 5

8-bromo-2,2-pentanooctanoic acid ethyl ester

To 25 ml of a 0.282 M solution of lithium diisopropylamide in tetrahydrofuran was added dropwise one g of cyclohexanecarboxylic acid ethyl ester in 5 ml of tetrahydrofuran at −70° C., the mixture was stirred at the same temperature for 50 minutes. To the mixture was added 1.86 g of 1,6-dibromohexane in 4 ml of tetrahydrofuran at −70° C. and the mixture stirred for 5 minutes.

To the mixture was added 2.68 ml of hexamethylphosphamide at the same temperature for 30 minutes and stirred at −30° C. for one hour. The extract was washed with water, a saturated aqueous solution of ammonium chloride and a saturated aqueous solution of sodium chloride, and dried over magnesium sulfate, and concentrated under reduced pressure. The residue was purified by column chromatography on silica gel using methylene chloride and cyclohexane (1:1) as an eluent to give 1.12 g of the title compound having the following physical characteristics:

TLC (benzene): Rf=0.74;
IR: $\nu$=2935, 2850, 1730, 1460, 1450, 1370, 1210, 1195, 1135, 1025 $cm^{-1}$;
NMR: $\delta$=4.03 (2H,q), 3.28 (2H,t), 2.8-0.75 (23H,m);
MS: m/e=320 (11), 318 (M+,11), 247 (14), 245 (17), 171 (13), 169 (12), 165 (11), 157 (13), 156 (100), 155 (13), 109 (17), 97 (23), 95 (20), 83 (40), 81 (28), 69 (25), 67 (17), 57 (11), 55 (33), 43 (12), 41 (28).

EXAMPLE 1

1-(7-ethoxycarbonyl-7,7-pentanoheptyl)imidazole

To 147 mg of sodium hydride (content 63%) suspended in 5 ml of N,N-dimethylformamide was added 263 mg of imidazole and the mixture was stirred at from 110° C. to 120° C. for 10 minutes. To the mixture was added 1.11 g of the bromide (prepared as described in Reference Example 5) in 3 ml of N,N-dimethylformamide, and the mixture was stirred at the same temperature for one hour and concentrated under reduced pressure. To the residue was added diethyl ether containing a small amount of water, and the solution was washed with a saturated aqueous solution of sodium chloride, dried over magnesium sulfate and concentrated under reduced pressure. The residue was purified by column chromatography on silica gel using a mixture of chloroform and methanol (9:1) as an eluent to give 967 mg of the title compound having the following physical characteristics:

TLC (chloroform:methanol=9:1): Rf=0.30

IR: $\nu$=3400, 2950, 2860, 1725, 1510, 1460, 1450, 1370, 1230, 1200, 1135, 1020, 900 cm$^{-1}$;

NMR: $\delta$=7.13 (1H,m), 7.0–6.6 (2H,m), 4.05 (2H,q), 3.83 (2H,t);

MS (%): m/e=307 (16), 306 (M+, 37), 305 (59), 260 (11), 250 (13), 233 (24), 232 (81), 152 (29), 151 (100), 138 (17), 137 (21), 124 (11), 123 (23), 110 (16), 109 (23), 96 (29), 95 (33), 83 (11), 82 (46), 81 (33), 69 (56), 68 (16), 67 (20), 55 (27), 54 (30), 53 (14), 41 (29).

EXAMPLE 2

1-(7-methoxycarbonyl-7-hydroxyheptyl)imidazole

The compound having the following physical characteristic was obtained using 1-bromo-7-hydroxyoctanoic acid methyl ester instead of the bromide used in Example 1, in the same manner as described in Example 1.

TLC (chloroform:methanol=9:1): Rf=0.57.

EXAMPLE 3

The following compounds were given using 1-hydroxypropioic acid ethyl ester or phenylacetic acid ethyl ester, respectively, instead of cyclohexanecarboxylic acid ethyl ester used in Reference Example 5, by the same procedure as described in Reference Example 5 and Example 1.

(a) 1-(7-ethoxycarbonyl-7-phenylheptyl)imidazole
TLC (chloroform:methanol=10:1): Rf=0.36.
(b) 1-(7-ethoxycarbonyl-7-hydroxymethylheptyl)imidazole
TLC (chloroform:methanol=9:1): Rf=0.59.

EXAMPLE 4

1-(7-carboxy-7,7-pentanoheptyl)imidazole hydrochloride

A mixture of 810 mg of the ester (prepared as described in Example 1), 4.2 ml of ethanol and 6.1 ml of a 2 N solution of sodium hydroxide was stirred at from 80° C. to 85° C. for 16 hours, and the reacting mixture was concentrated under reduced pressure, and the residue was washed twice with chloroform, and the solution was concentrated by azeotropic distillation with t-butanol. The residue was adjusted to pH 3 with a 3 N solution of hydrochloric acid, and concentrated under reduced pressure and concnetrated by azeotropic distillation with t-butanol.

To the residue was added a mixture of ethanol and diethyl ether (95:5), and the resulting crystals were washed with diethyl ether to give 140 mg of the title compound having the following physical characteristics:

melting point: 158° C.–160° C.;

TLC (ethyl acetate:water:acetic acid=3:1:1): Rf=0.67;

IR: $\nu$=3400, 3100, 3045, 2945, 2855, 1710, 1580, 1540, 1470, 1450, 1410, 1385, 1295, 1215, 1180, 1170, 1135, 1085 cm$^{-1}$;

NMR: $\delta$=8.90–8.50 (1H,m), 7.95–7.10 (2H,m), 4.26 (2H,t).

EXAMPLE 5

1-(7-carboxy-7-phenylheptyl)imidazole hydrochloride

A mixture of 119 mg of the ester (prepared as described in Example 3(a)), one ml of ethanol and 0.38 ml of a 2 N solution of sodium hydroxide was refluxed for 4 hours and 5 ml of water was added thereto, and the mixture was concentrated under reduced pressure. Water was added to the residue and the solution was extracted with diethyl ether. The aqueous layer was acidified to pH 1 with a dilute solution of hydrochloric acid, and concentrated under reduced pressure and concentrated by azeotropic distillation with t-butanol. The residue was diluted with absolute ethanol and insoluble materials were removed off, and the solution was concentrated under reduced pressure. Repeating the same procedure, 56 mg of the title compound having the following physical characteristics was obtained.

IR: $\nu$3600–2300, 1709, 1572, 1448, 1186, 1083, 721, 696 cm$^{-1}$;

NMR (D$_2$O solution): $\delta$=8.72 (1H,m), 7.54 (1H,m), 7.48 (1H,m), 7.37 (5H,s), 4.21 (2H,t)

MS (%): m/e=242 (57), 151 (49), 138 (41), 137 (58), 96 (57), 95 (95), 91 (48), 82 (100).

EXAMPLE 6

The following compounds were prepared using the ester prepared in Example 2 and Example 3(b) instead of the ester using in Example 4, by the same procedure as described in Example 4, provided that the process of purification was not done.

(a) 1-(7-carboxy-7-hydroxyheptyl)imidazole hydrochloride
TLC (ethyl acetate:water:acetic acid=3:1:1): Rf=0.25;
IR: $\nu$=3350, 2950, 2870, 1750, 1590, 1560 cm$^{-1}$;
NMR (D$_2$O solution): $\delta$=8.8–8.6 (1H,m), 7.6–7.3 (2H,m) 4.4–4.05 (3H,m), 2.3–1.0 (10H,m).

(b) 1-(7-carboxy-7-hydroxymethylheptyl)imidazole hydrochloride
TLC (ethyl acetate:water:acetic acid=3:1:1): Rf=0.5;
IR: $\nu$=3400, 3150, 2500, 1720 cm$^{-1}$;
NMR (D$_2$O solution): $\delta$=8.9–8.7 (1H,m), 7.7–7.45 (2H,m), 4.3 (2H,t), 2.8–2.5 (1H,m), 2.2–1.1 (10H,m).

EXAMPLE 7

1-(7-carboxy-7-chloroheptyl)imidazole hydrochloride

To 140 mg of 1-(7-carboxy-7-hydroxyheptyl)imidazole hydrochloride (prepared in Example 6(a)) was added dropwise 0.193 ml of thionyl chloride at from 0° C. to 3° C., and the mixture was stirred at room temperature overnight, and concentrated under reduced pressure. Ice was added to the obtained residue, and the mixture was stirred for 5 minutes, and concentrated under reduced pressure. A small amount of water was added to the residue, and insoluble materials were removed off, and the solution thus obtained was concentrated under reduced pressure to give 149 mg of the title compound having the following physical characteristics:

IR: ν=3700-2400, 1740, 1580, 1550, 1460, 1190 cm$^{-1}$;

NMR (DMSO-D$_6$ solution):=9.3 (1H,s), 7.95-7.6 (2H,d), 4.7-4.0 (3H,m).

EXAMPLE 8

1-(7-carboxy-7-octenyl)imidazole hydrochloride

To 180 mg of 1-(7-carboxy-7-hydroxymethylheptyl-)imidazole hydrochloride (prepared in Example 6(b)) was added 2 or 3 drops of phosphoric acid, and the mixture was reacted under reduced pressure at 160° C. for 5 hours. The reaction mixture was purified by column chromatography on cellulose using a mixture of n-butanol, water and acetic acid (8:10:1), and the obtained fraction was adjusted to pH 8 with a 1 N solution of sodium hydride in order to remove the contaminated phosphoric acid, and the resulting crystals was removed off. The same purification by column chromatography on cellulose was repeated to give 78 mg of the title compound having the following physical characteristics:

TLC (ethyl acetate:water:acetic acid=3:1:1): Rf=0.46;

NMR (D$_2$O solution): δ=8.83-8.65 (1H,m), 7.62-7.38 (2H,m), 6.23-6.09 (1H,m), 5.75-5.6 (1H,m), 5.27 (2H,t), 2.46-2.1 (2H,m), 2.1-1.02 (8H,m).

EXAMPLE 9

Ten g of 1-(7-carboxy-7-octenyl)imidazole hydrochloride, 10 mg of cellulose calsium gluconate (disintegrator), 2 mg of magnesium stearate (lubricating agent) were mixed and punched out in a conventional manner to obtain tablets each containing 100 mg of the active ingredient.

We claim:

1. An imidazole of the general formula:

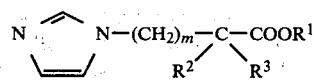

wherein m represents an integer of 4 to 9, R$^1$ represents a hydrogen atom or a straight- or branched-chain alkyl group containing from 1 to 12 carbon atoms, and one of R$^2$ and R$^3$ represents a hydrogen atom, and the other represents a halogen atom or a phenyl group, or R$^2$ and R$^3$ together represent —(CH$_2$)$_n$—, in which n represents an integer of 4 to 6, or represent =CH$_2$, or pharmaceutically acceptable non-toxic salts thereof.

2. A compound according to claim 1 wherein R$^1$ represents a hydrogen atom, a methyl group or a ethyl group.

3. A compound according to claim 1 wherein R$^1$ represents a hydrogen atom.

4. A compound according to claim 1 wherein m represents an integer of 5 to 7.

5. A compound according to claim 1 wherein m represents 6.

6. A compound according to claim 1 which is 1-(7-carboxy-7-chloroheptyl)imidazole or its hydrochloride.

7. A compound according to claim 1 which is 1-(7-carboxy-7-phenylheptyl)imidazole or its hydrochloride.

8. A compound according to claim 1 which is 1-(7-carboxy-7,7-pentanoheptyl)imidazole or its hydrochloride.

9. A compound according to claim 1 which is 1-(7-carboxy-7-octenyl)imidazole or its hydrochloride.

10. A pharmaceutically acceptable non-toxic salt of an imidazole derivative according to claim 1.

11. A thromboxane A$_2$ inhibiting composition which comprises, as an active ingredient, an effective amount of at least one compound of the general formula (I) depicted in claim 1, wherein various symbols are as defined in claim 1, or a pharmaceutically acceptable non-toxic salt thereof, together with a pharmaceutical carrier or coating.

12. A method of treating diseases and disorders caused by thromboxane A$_2$ which comprises administering an effective amount of a compound as claimed in claim 1 or a pharmaceutically acceptable non-toxic salt thereof.

* * * * *

UNITED STATES PATENT AND TRADEMARK OFFICE
CERTIFICATE OF CORRECTION

PATENT NO. : 4,346,099
DATED : August 24, 1981
INVENTOR(S) : T. Tanouchi et al

It is certified that error appears in the above—identified patent and that said Letters Patent is hereby corrected as shown below:

On the title page

Please insert the following under "[22] Filed: Sep. 22, 1981:"

--[30] Foreign Application Priority Data

Sept. 22, 1980 [JP] Japan  55-130643--.

Signed and Sealed this

Fourteenth Day of December 1982

[SEAL]

Attest:

GERALD J. MOSSINGHOFF

Attesting Officer

Commissioner of Patents and Trademarks